United States Patent [19]

Nadzan et al.

[11] Patent Number: 4,572,907

[45] Date of Patent: Feb. 25, 1986

[54] HIGH CALORIC PRODUCT FOR I.V. ADMINISTRATION

[75] Inventors: Alex M. Nadzan, Gurnee; André G. Pernet, Lake Bluff, both of Ill.; Stephen Hanessian, Beaconsfield, Canada

[73] Assignee: Abbott Laboratories, North Chicago, Ill.

[21] Appl. No.: 592,320

[22] Filed: Mar. 22, 1984

[51] Int. Cl.$^4$ .............................................. A61K 31/72
[52] U.S. Cl. ........................................ 514/25; 514/23; 536/1.1; 536/4.1; 536/18.2; 536/119
[58] Field of Search ................. 536/1.1, 4.1, 119, 18.2; 514/23, 25

[56] References Cited

U.S. PATENT DOCUMENTS 3,694,480  9/1972  Omietanski ........................ 536/1.1
4,182,756  1/1980  Ramsay et al. .................... 536/1.1
4,238,473  12/1980  Lemieux et al. .................. 536/1.1

Primary Examiner—Johnnie R. Brown
Assistant Examiner—Elli Peselev
Attorney, Agent, or Firm—Alan R. Thiele; Michael J. Roth; Martin L. Katz

[57] ABSTRACT

This invention relates to a product which will provide a high caloric source upon I.V. administration. More particularly, this invention relates to glucosyl esters of malonic acids and substituted malonic acid derivatives which will permit the assimilation of glucose into the body at high concentrations but with low toxicity.

26 Claims, No Drawings

HIGH CALORIC PRODUCT FOR I.V. ADMINISTRATION

BACKGROUND OF THE INVENTION

Providing adequate nutrition via the parenteral route requires administration of both lipids and carbohydrates in sufficient quantities within an acceptable volume of solution. Most technical problems have been solved in conjunction with the administration of lipids. This is evidenced by products such as Liposyn fat emulsion which can deliver the required number of fat calories. However, administration of the desired number of carbohydrate calories via the peripheral route remains inadequate. The main reason is that an isotonic solution of glucose such as 5% dextrose only delivers 170 Kcal/liter, while the desired daily regime is 850 Kcal/liter. One may consider three alternatives:

1. Increase the volume of solution by 5 times. This is obviously unacceptable, as the total volume of fluid permitted per day is 3 liters.

2. Increase the concentration of the solution by 5 times. This results in a hypertonic solution which would damage peripheral veins when administered intravenously.

3. Use a polymer of glucose. This has been studied and possesses the advantage of delivering 3-7 glucose units in one molecule, thereby increasing the theoretical caloric content while maintaining an isotonic osmolarity solution.

One limitation of using such a glucose polymer is that the human body apparently has a limited capacity to hydrolyze efficiently the glycosidic linkages which interconnect the glucose units. This results in a loss of calories as a consequence of excretion of polymer fragments such as maltose in the urine.

It has now been found that this problem of limited hydrolysis and excretion can be circumvented by using hybrid ester oligomers and/or polymers of the general formula:

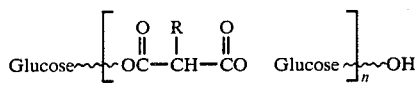
(I)

wherein n is an integer of 1 to 20 and R is hydrogen or an alkyl or alkenyl group having 1 to 20 carbon atoms. The ester linkages coupling the glucose and malonate units in I may be at any of the available glucose hydroxyl functions and may vary within different glucose units of a given polymer or polymer mixture. Those compounds where the alkyl or alkenyl group carbon has an even number of carbon atoms are preferred. Compounds of the foregoing formula have the advantage of providing ester linkages which are readily hydrolyzed by esterases widely distributed in human tissues.

These malonic acid derivatives were chosen because they would be decarboxylated in vivo through enzymes like palmitate synthetase which exists in vertebrates. This is illustrated as follows:

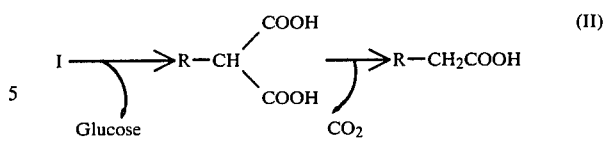

wherein I is as previously stated and R is the same in Formulae I and II. The product of decarboxylation (II) is a natural fatty acid; therefore, a nontoxic food constituent which also can provide considerable caloric value.

The choice of the R substituent provides flexibility in adjusting the total caloric content from the lipid part. For example, R could be an unsaturated fatty acid side chain of sufficient carbon atoms so that linoleic acid results from decarboxylation, if this feature is of advantage in the diet of the recipient. The number of glucose units provides flexibility from the carbohydrate standpoint.

Another advantage of the compounds of this invention are their low toxicity. For example, di-(1,1'-D-glucopyranosyl)ethylmalonate, when tested in mice, exhibited an $LD_{50}$ of 9.70 g/kg.

The compounds as represented by Formula I may be prepared readily from known materials. Compounds containing two glucose moieties and one malonate unit (Formula I, n=1) can be prepared by reacting an appropriately protected monohydroxy glucose with an activated malonic acid derivative wherein R is stated in Formula I to give a protected malonyl diester which, upon subsequent removal of the glucose protecting groups, affords the desired diglucosyl malonate (Formula I, n=1) as outlined below:

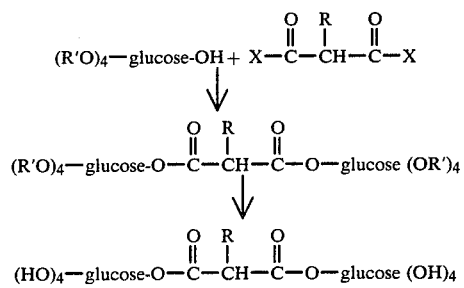

For such reactions, benzylether substituted monohydroxyglucose derivatives ($R'=CH_2$-phenyl) are preferred as they can be removed under neutral catalytic hydrogenolysis conditions, however, other substituted glucose derivatives may be utilized providing the protecting groups can be removed under conditions which do not cleave the glucose-ester bond. Such protected derivatives will be evident by those skilled in the art.

Compounds containing three glucose units and two malonate derivatives (Formula I, n=2) may be prepared by condensing two moles of a protected glucosyl malonate monoester with one mole of a suitably protected dihydroxyglucose, followed by removal of glucose protecting groups under mild conditions as indicated by the following equation:

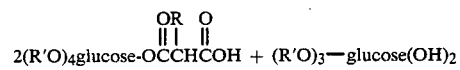

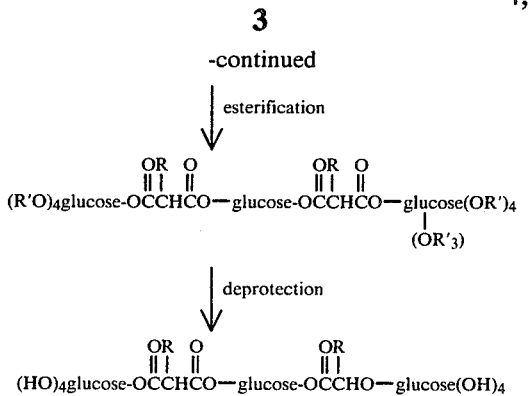

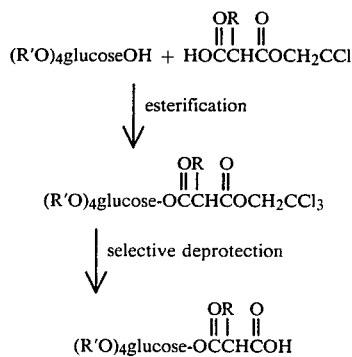

The required glucosylmalonate monoesters are prepared readily from a suitably protected monohydroxy glucose and a malonate monoester derivative such as 2,2,2-trichloroethyl malonate, followed by selective removal of the nonglucosyl ester as shown below:

$$(R'O)_4\text{glucoseOH} + \text{HOCCHCOCH}_2\text{CCl}_3$$
$$\overset{OR}{\underset{}{|}}\overset{O}{\underset{}{||}}$$

↓ esterification $$(R'O)_4\text{glucose-OCCHCOCH}_2\text{CCl}_3$$
$$\overset{OR}{\underset{}{|}}\overset{O}{\underset{}{||}}$$

↓ selective deprotection $$(R'O)_4\text{glucose-OCCHCOH}$$
$$\overset{OR}{\underset{}{|}}\overset{O}{\underset{}{||}}$$

Preferred esterification conditions for these condensations are a modification of the carbodiimidedimethylaminopyridine procedures described by B. Neises and W. Steglich, Angew. Chem. Int. Ed. Engl. 1978, 17, 522–524 and by A. Hassner and V. Alexanian, Tetrahedron Lett. 1978, 4475–4478.

The following examples are set forth for the purpose of illustrating specific compounds of the present invention. They should not be construed to limit the invention to the precise ingredients, proportions, temperatures or other conditions.

In the following examples, all temperatures are indicated as Centigrade.

EXAMPLE 1

Di-(2,3,4,6-tetra-O-benzyl-D-glucopyranosyl)n-butyl-malonates n-Butylmalonyl dichloride was initially prepared from n-butylmalonic acid (m.p. 98°–99° from benzene) by reaction with thionyl chloride (b.p. 84°–86°/15 mm Hg.). Under argon atmosphere, a solution of n-butylmalonyl dichloride (300 mg, 1.5 mmol) in dry methylene chloride (5 mL) was added dropwise, over a period of 30 minutes, to a stirred solution of commercially available 2,3,4,6-tetra-O-benzyl-D-glucose (1.62 g, 3 mmol) and dry triethylamine (430 mg, 4.3 mmol) in dry methylene chloride (35 mL) cooled at −30°. After completion of the addition, the solution was further stirred at −30° for two hours, then warmed at room temperature and absorbed on silica gel (60–200 mesh, 6 g). Column chromatography over silica gel (100 g) eluted with 1:2 mixture of ethyl acetate-hexanes (1000 mL) afforded the title compound (1.58 g, 1.3 mmol, 88% yield) as a viscous heavy oil having a molecular weight of 1205. The following analysis confirmed the title compound: IR (CCl$_4$): 3050, 3025, 2900, 2850, 1750 (s), 1500, 1460, 1100 (vs) cm$^{-1}$; NMR (CDCl$_3$): δ 7.33 (s, C$_6$H$_5$), 6.50 (m, H-1, α-anomers), 5.70 (m, H-1, β anomers), 4.95–4.44 (m), 3.99–3.55 (m), 1.95–1.27 (2m, 3 CH$_2$), 0.81 (m, CH$_3$).

EXAMPLE 2

Di-(1,1'-D-glucopyranosyl)n-butylmalonates

A solution of the compound prepared in Example 1 (420 mg, 0.348 mmol) in 6 mL of dry tetrahydrofuran (THF) was shaken for a few minutes with 100 mg charcoal (previously purified by neutral Norit washing twice with acetic acid and four times with diethyl ether and dried in vacuo over KOH) and subsequently filtered. The charcoal was further washed twice with 2 mL of THF. The filtrates were combined and then hydrogenated in the presence of 10% palladium on charcoal (200 mg) during 22 hours. The mixture was filtered and the catalyst was washed with two portions (3 mL) of a 1:1 mixture of THF-MeOH. Evaporation in vacuo of the combined filtrates afforded the title compound (182 mg, 0.379 mmol) as a fluffy white solid having a molecular weight of 480. The following analysis confirmed the title compound: I.R. (Nujol) 3350 (v. br), 1760–1730 cm$^{-1}$; NMR (D$_2$O, chemical shifts relative to HOD, 4.75) δ6.12 (br.s, H-1, α-anomers), 5.58 (d, J=7 Hz, β-anomers), 3.85–3.30 (m), 1.86–1.25 (2m, 3 CH$_2$), 0.80 (m, CH$_3$) anomeric ratio α:β=1.4:1.

The compound of this Example was found to be stable at 0° for substantially long periods of time. NMR and TLC analysis showed no noticeable degradation of the compound after one month. It appeared also stable in water (15 mg/mL) at room temperature for one week (TLC analysis). Partial hydrolysis into D-glucose was noted after one month.

Heating the aqueous solution at 60° caused some hydrolysis after about two hours at which time, the formation of D-glucose started to appear (NMR and TLC analysis). Unexpectedly, the hydrolysis of the β-anomers appeared faster than that of the α-anomers. After 36 hours, the β-anomers completely disappeared while some α-anomers were still present. No acyl-migration products were detected.

On heating the solid compound at 60°, a slow degradation was noted after 3 hours, with the formation of D-glucose and unidentified decomposition products (trail on the TLC plates).

EXAMPLE 3

Di-(2,3,4,6-tetra-O-benzyl-D-glucopyranosyl)ethylmalonates

Initially, ethylmalonyl dichloride was prepared from ethylmalonic acid (m.p. 95°, from benzene) by reaction with thionyl chloride in the manner indicated in Example 1. Under argon atmosphere, a solution of ethylmalonyl dichloride (341 mg, 2.02 mmol) in dry methylene chloride (5 mL) was added dropwise, over a period of 30 minutes to a stirred solution of 2,3,4,6-tetra-O-benzyl-D-glucose (2.16 g, 4 mmol) and dry triethylamine (431 mg, 4.3 mmol) in methylene chloride (35 mL), cooled at −30°. After completion of the addition, the solution was further stirred at −30° for two hours, then warmed at room temperature and absorbed on silica gel (60–200 mesh, 6 g). Column chromatography over silica gel (130 g) eluted with a 1:2 mixture of ethyl acetate-hexanes (1200 mL) afforded the title compound (2.17 g, 1.84 mmol, 91% yield) as a viscous oil having a molecular weight of 1177. The following analysis confirmed the title compound: IR (CCl$_4$) 3050, 3025, 2900, 2850, 1770 (shoulder), 1750 (s), 1500, 1460, 1100 (vs) cm$^{-1}$; NMR (CDCl$_3$) $\delta$7.33 (s, C$_6$H$_5$), 6.47 (m, H-1, $\alpha$-anomers), 5.71 (m, H-1, $\beta$-anomers), 4.95–4.40 (m), 3.93–3.42 (m), 2.01 (app. sept, J=7 Hz, CH$_2$), 0.98 (app. t, J=7 Hz, CH$_3$).

EXAMPLE 4

Di-(1,1'-D-glucopyranosyl)ethylmalonates

A solution of the compound prepared in Example 3 (417 mg, 0.354 mmol) in dry THF (6 mL) was shaken for a few minutes with 100 mg of charcoal previously (purified by neutral Norit washing as indicated in Example 2), then filtered. The charcoal was washed twice with THF (2 mL) and the combined filtrates were hydrogenated in the presence of 10% palladium on charcoal (200 mg) during 21 hours. The mixture was then filtered and the catalyst was washed with two portions (3 mL) of a 1:1 mixture of THF-MeOH. The filtrates were evaporated in vacuo to give the title compound (189 mg, 0.414 mmol) as a colorless oil containing methanol and some D-glucose having a molecular weight of 456. The following analysis confirmed the title compound: NMR (D$_2$O, chemicals shifts relative to HOD, 4.75): $\delta$6.11 (br.s., H-1, $\alpha$-anomers), 5.50 (d, J=7 Hz, H-1, $\beta$-anomers), 3.75–3.19 (m), 1.78 (m, CH$_2$), 0.87 (t, J=7 Hz, CH$_3$); anomeric ratio $\alpha$:$\beta$=3:1.

EXAMPLE 5

Di-6,6'-(benzyl-2,3,4-tri-O-benzyl-$\alpha$-D-glucopyranosyl)malonate

A solution of malonyl dichloride (Aldrich Chemical Co., redistilled, 0.2 mL, 2 mmol) in methylene chloride (5 mL) was added dropwise to a solution of benzyl 2,3,4-tri-O-benzyl-$\alpha$-D-glucopyranoside (2.16 g, 4 mmol), prepared by the method of A. Lubineau, et al., Carbohydr. Res., 1976, 46, 143 and S. David, Tetrahedron, 1978, 34 229, and triethylamine (560 mg, 5.6 mmol) in methylene chloride (25 mL) cooled at −30° under argon atmosphere. After completion of the addition, the orange solution was further stirred at −30° for 30 minutes, then warmed at room temperature. Silica gel (230–400 mesh, 5 g) was added and the mixture evaporated to dryness under reduced pressure. The powder was poured at the top of a Flash-chromatography column (30 mm diameter, 23 cm of silica gel). Elution with a 3:1 mixture of hexane-ethyl acetate afforded the title compound (1.67 g, 1.45 mmol, 72%, evaporated in vacuo at 40°) as a colorless syrup: IR (CCl$_4$): 3070, 3050, 3025, 2950, 2925, 2875, 1760 (shoulder), 1745 (s), 1100 (s) cm$^{-1}$; NMR (CDCl$_3$) $\delta$7.42 and 7.35 (2 s, 40 H, aromatic protons), 5.15–3.50 (m, 30 H, sugar skeleton and benzyl protons), 3.40 (s, 2 H malonyl protons).

EXAMPLE 6

Di-(6,6'-glucopyranosyl)malonate

A solution of the compound prepared in Example 5 (355 mg, 0.309 mmol) in a 1:1 mixture of dry THF-EtOH (10 mL) was hydrogenated under atmospheric pressure at room temperature, in the presence of 10% palladium-on-charcoal (180 mg) during 22 hours. The catalyst was filtered and washed with a 1:1 mixture of THF-MeOH (2×3 mL). The filtrates were evaporated under reduced pressure (20 mm Hg, 30°) then dried in vacuo. The residue (135 mg) was dissolved in water (2 mL) and filtered over purified celite. The celite was washed with water (2×0.5 mL) and the combined aqueous solutions were lyophilized to afford the title compound as a light white powder (121 mg, 0.283 mmol, 91%); mp: soften at 85°–90° C. with gas evolution starting at 110° C.; [$\alpha$]$_D$ (C 0.51, H$_2$O) initial +56.2°., equilibrated +51.9°; IR (Nujol): 3550–3200 (v br), 1760–1720 (br s) cm$^{-1}$; NMR (D$_2$O, 90 MHz, chemical shifts relative to HOD, 4.75) 5.17 (d, J=4 Hz, H-1, $\alpha$-anomers), 4.60 (d, J=8 Hz, H-1, $\beta$ anomers), 4.35 (m, 4 H, H-6), 4.05–3.35 (m, 8 H, H-2,3,4,5, sugar protons) 3.26 (s, 2 H malonyl protons).

EXAMPLE 7

2,3,4,6-Tetra-O-benzyl-D-glucopyranosyl hydrogen malonate (1)

A mixture of finely powdered malonic acid (10.4 g, 0.1 mol), 2,2,2-trichloroethanol (9.6 mL, 0.1 mol) and p-toluenesulfonic acid monohydrate (570 mg, 3% in benzene (30 mL) was stirred under azeotropic reflux for 26 hours, then cooled at room temperature. The unreacted malonic acid (4.6 g) was filtered and washed with benzene (2×10 mL). Water (50 mL) was added to the filtrate followed by portionwise addition of sodium bicarbonate until a basic pH was reached. The aqueous phase was decanted, washed with ether (3×50 mL), then acidified with concentrated aqueous HCl and extracted with methylene chloride (4×50 mL). The combined extracts were washed with brine (25 mL), dried over MgSO$_4$, filtered and evaporated in vacuo to give 2,2,2-trichloroethyl hydrogen malonate (4.34 g, 18.4 mmol, 18%) that slowly crystallized; m.p. 42°–43°; NMR (CDCl$_3$): $\delta$11.0 (S, CO$_2$H), 4.83 (S, —OCH$_2$CCl$_3$), 3.61 (S, —O$_2$C—CH$_2$CO$_2$—).

Dicyclohexylcarbodiimide (305 mg, 1.47 mmol) was added to a solution of 2,3,4,6-tetra-O-benzyl-D-glucopyranose (810 mg, 1.5 mmol), 2,2,2-trichloroethyl hydrogen malonate (330 mg, 1.4 mmol) and pyridine (196 mg, 2.48 mmol) in dry methylene chloride (6 mL). A white precipitate appeared almost immediately and a slight temperature increase was noticed. The mixture was stirred further for one hour, then diluted with ether (10 mL) and filtered. The solid was washed with ether (2×5 mL) and the filtrates were evaporated under reduced pressure in the presence of silica (2 g). Chromatography over silica gel (60–200 mesh, 40 g, elution with ether-hexanes, 1:1.5) afforded 2,3,4,6-tetra-O-benzyl-D-glucopyranosyl 2,2,2-trichloroethyl malonate 2 (929 mg, 1.22 mmol, 87%) as a viscous colorless syrup; NMR (CDCl$_3$, 90 MHz): $\delta$7.37+7.32 (aromatic protons), 6.43 (d, J=2 Hz, H-1, $\alpha$-anomer), 5.71 (d, J=7 Hz, H-1, $\beta$-anomer), 4.92–4.42 (m, benzylic protons) with a high singlet at 4.78 (OCH$_2$Cl$_3$), 3.87–3.40 (m, sugar skeleton and malonyl protons); aromatic ratio, $\alpha$:$\beta$=1.7 IR (CCl$_4$): 3090, 3075, 3024, 2925, 2875, 1770 (s), 1755 (s), 1100 (s) cm$^{-1}$.

EXAMPLE 8

1,6-Di-O-(2,3,4,6-tetra-O-benzyl-D-glucopyranosyl-1-O-malonyl)-2,3,4-tri-O-benzyl-D-glucopyranose Crude 2,3,4,6-tetra-O-benzyl-D-glucopyranosyl hydrogen malonate (1) (757 mg, 1.21 mmol) was dissolved in dry methylene chloride (5 mL) and treated successively with 2,3,4-tri-O-benzyl-D-glucopyranose (217 mg, 0.482 mmol, 0.4 eq; Ref. R. Eby, et al, Carbohydr. Res. 1979, 73, 273–276), 4-dimethylaminopyridine (29 mg, 0.23 mmol) and dicyclohexylcarbodiimide (106 mg, 1 mmol). A white precipitate appeared almost immediately and a slight temperature increase was noticed. After 1 hour stirring at room temperature, additional dicyclohexylcarbodiimide (43 mg, 0.20 mmol) was added. After a further 30 min. stirring, the mixture was diluted with ether (15 mL) and filtered. The white solid (236 mg) was washed with ether (2×5 mL) and the filtrate was evaporated under reduced pressure with silica (1.8 g). The resulting powder was placed at the top of a flash-chromatography column (30 mm diam, 16 cm of silica). Elution with a 1:3 (300 mL), followed by a 1:2.5 (300 mL) mixture of ethyl acetate-hexanes afforded the title compound (625 mg, 0.375 mmol, 77% from the diol 9, 63% overall yield) as a colorless oil, dried in vacuo at 40°. The title compound had the following physical properties: NMR (CDCl$_3$, 90 MHz): $\delta$7.34 (aromatic protons), 6.40 (br s, H-1 $\alpha$-anomers), 5.68 (br d, J=7 Hz, H-1, $\beta$-anomers), 4.93–4.37 and 3.97–3.33 (2 m, benzylic, sugars skeleton and malonyl protons); anomeric ratio, $\alpha:\beta=1.4:1$; IR (CCl$_4$): 3090, 3075, 3040, 2920, 2875, 1750 (s), 1100 (s) cm$^{-1}$.

EXAMPLE 9

1,6-Di-O-(1-O-D-glucopyranosyl malonyl)-D-glucopyranose

A solution of the title compound of Example 8 (573 mg, 0.344 mmol) was dissolved in a mixture of dry THF (15 mL) and EtOH (15 mL) and treated with hydrogen at atmospheric pressure in the presence of 20% palladium on charcoal (500 mg) for 26 hours. The mixture was then filtered over celite and the catalyst was washed with a 1:1 mixture of THF-MeOH (2×5 mL). The combined filtrates were evaporated under reduced pressure at room temperature and dried in vacuo. The resulting white solid (245 mg) was redissolved in water (2 mL) and filtered over celite. The celite was washed with water (3×2 mL) and the filtrates were freeze-dried to afford the title compound (230 mg, 0.340 mmol, 98%) as a light white powder; NMR (D$_2$O, 90 MHz, chemical shifts relative to HOD, 4.75 ppm): $\delta$6.12 (br s, H-1, $\alpha$-1-O-acyl sugars), 5.60 (br d, J=7 Hz, H-1, $\beta$-1-O-acyl sugars), 4.40 (m, H-6, 6-O-acyl sugar), 3.81–3.37 (m, sugars skeleton and malonyl protons); anomeric ratio, $\alpha:\beta=1.3:1$; IR (KBr): 3400 (br), 2925 (m), 1750 (s), 1640 (m), 1100 (s) cm$^{-1}$; m.p. (hot stage apparatus): the compound softens and partially melts at 105°–110° with gas evolution starting at 135°–140°; $[\alpha]_D +71° \rightarrow +34°$ (c 0.50, H$_2$O). Analysis Calcd. for C$_{24}$H$_{36}$O$_{22}$ (M.W. 676.16): C, 42.59; H, 5.36. Found: C, 42.48; H, 5.49.

EXAMPLE 10

[Benzyl 2,3,4-tri-O-benzyl-$\alpha$-D-glucopyranosyl]hydrogen malonate

To a solution of benzyl 2,3,4-tri-O-benzyl-$\alpha$-D-glucopyranoside (810 mg, 1.5 mmol), 2,2,2-trichloroethyl hydrogen malonate (330 mg, 1.4 mmol), prepared in the first paragraph of Example 7, and pyridine (180 mg, 2.27 mmol) in dry methylene chloride (6 mL) was added dicyclohexylcarbodiimide (296 mg, 1.43 mmol). A white precipitate appeared immediately. The mixture was stirred at room temperature for one hour, then diluted with ether (15 mL) and filtered. The solid was washed with ether (2×5 mL) and the filtrate was evaporated under reduced pressure with silica (2 g). Rapid chromatography on regular silica (60–200 mesh, 50 g, elution with ethyl acetate-hexanes, 1:3.5) afforded the trichloroethyl ester (927 mg, 1.22 mmol, 87%) as a viscous colorless syrup; NMR (CDCl$_3$, 90 MHz): $\delta$7.43, 7.41, 7.37, 7.35 (aromatic protons), 5.15–3.39 (m, benzylic and sugar skeleton protons); 4.78 (s, CH$_2$CCl$_3$) and 3.53 (s, O$_2$CCH$_2$CO$_2$); IR (CCl$_4$): 3090, 3075, 3040, 2925, 2875, 1770 (s), 1750 (s), 1100 (s) cm$^{-1}$.

To a solution of the above trichloroethyl ester (927 mg, 1.22 mmol) in THF (9 mL) were added zinc dust (1.8 g) and 1M aqueous KH$_2$PO$_4$ solution (1.8 mL). The mixture was stirred vigorously at room temperature for 65 minutes. The organic layer was then decanted and the lower layer (zinc residue) was extracted with ether (2×10 mL). The combined organic phases were chilled at 0° and washed successively with cold 10% aqueous HCl (2×5 mL), water (5 mL) and brine (5 mL), then dried over MgSO$_4$. After filtration and washing of the drying agent with ether (2×5 mL), the filtrate was stirred with an acidic resin (DOWEX-H+ 50W-x8, 4 mL) for 10 minutes, then refiltered and evaporated in vacuo (40°) to give the title compound as a thick colorless syrup (726 mg, theoretically 1.16 mmol of crude acid).

EXAMPLE 11

1,6-Di-O-[6-O-(benzyl-2,3,4-tri-O-benzyl-$\alpha$-D-glucopyranosyl)malonyl]2,3,4-tri-O-benzyl-D-glucopyranose The crude title compound of Example 10 (726 mg, theoretically 1.16 mmol of crude acid) was redissolved in dry methylene chloride (5 mL) to which were successively added 2,3,4-tri-O-benzyl-D-glucopyranose (208 mg, 0.462 mmol), 4-dimethylaminopyridine (24 mg, 0.2 mmol) and dicyclohexylcarbodiimide (198 mg, 0.959 mmol). A white precipitate started to appear almost immediately. After one hour stirring, supplementary dicyclohexylcarbodiimide (41 mg, 0.198 mmol) was introduced. After a further 30 minute stirring, the mixture was diluted with ether (15 mL) and filtered. The white solid (233 mg) was washed with ether (10 mL) and the filtrate was evaporated under reduced pressure with silica (1.8 g). The powder was placed at the top of a flash-chromatography column (30 mm diam, 15 cm of silica 230–400 mesh) and eluted with a 1:2.5 (400 mL) followed by a 1:2 (200 mL) mixture of ethyl acetate-hexane. The appropriate fractions were pooled, evaporated and submitted to a second chromatography using a 12:1 mixture of benzene-ethyl acetate as eluent (500 mL) to afford the title compound (636 mg, 0.381 mmol, 62% overall yield) as a glassy colorless syrup after drying in vacuo at 40°; NMR (CDCl$_3$, 90 MHz) $\delta$7.41+7.33 (aromatic protons), 6.33 (d, J=3 Hz, H-1, $\alpha$-1-O-acyl sugar), 5.66 (d, J=8 Hz, H-1, $\beta$-1-O-acyl sugar), 5.14–3.36 (benzylic, sugars skeleton and malonyl protons); anomeric ratio, $\alpha:\beta=1.5:1$; IR (CCl$_4$): 3090, 3075, 3040, 2925, 2875, 1750 (s), 1100 (s) cm$^{-1}$.

EXAMPLE 12

1,6-Di-O-(6-O-D-glucopyranosyl malonyl)-D-glucopyranose

A solution of the title compound of Example 11 (600 mg, 0.360 mmol) in a mixture of dry THF EtOH (30 mL, 7:1) was hydrogenated at atmospheric pressure in the presence of 20% Pd-on-charcoal (500 mg). After 30 hours, the mixture was filtered over celite. The catalyst was washed with a 1:1 mixture of THF-MeOH (2×5 mL). The combined filtrates were evaporated under reduced pressure (temperature kept below 30°) and dried in vacuo. The white solid (249 mg) was redissolved in water (2 mL) and filtered over celite. The celite was washed with water (2×2 mL) and the combined filtrates were freeze-dried to give the title compound (238 mg, 0.352 mmol, 97%) as a white powder; NMR (D$_2$O, 90 MHz, Chemical shifts relative to HOD, 4.75 ppm): δ6.10 (d, J=2 Hz, H-1, α-1-O-acyl sugar), 5.59 (d, J=7 Hz, H-1, β-1-O-acyl sugar), 5.16 (d, J=3 Hz, H-1, α-free sugar), 4.59 (d, J=8 Hz, H-1, β-free sugar), 4.37 (m, H-6 sugars protons), 4.40–3.07 (m, H-2,3,4,5 sugars and malonyl protons); 1-O-acyl sugar anomeric ratio, α:β=1.6:1; IR (KBr): 3400 (br), 2925 (m), 1745 (s), 1640 (m), 1100 (s) cm$^{-1}$; m.p. (hot stage apparatus): the compound softens and partially melts at 105°–110° with gas evolution starting at 140°–140°; [α]$_D$+52.4°→+38.6° (C 0.50, H$_2$O); Analysis Calcd. for C$_{24}$H$_{36}$O$_{22}$ (M.W. 676.16): C, 42.59; H, 5.36. Found: C, 42.48; H, 5.49.

The D-glucopyranosyl malonates prepared in Examples 2, 4, 6, 9 and 12 represent low molecular weight nutrients wherein n in Formula I is equal to one or two. These relatively low molecular weight derivatives may be present in polymeric mixtures of I wherein n is an integer greater than one. Such polymers may be prepared by esterification of malonic acid or a substituted malonic acid with a bifunctional D-glucose such as 2,3,4-tri-O-benzyl-D-glucopyranose, followed by removal of the benzyl protecting groups by catalytic hydrogenolysis.

Alternatively, similar polymer mixtures may be obtained directly from D-glucose and a malonic acid derivative. Mixtures of compounds as represented by Formula I also can be prepared where R is H or different alkyl or alkenyl groups in the same mixture. The average molecular weight (n in Formula I) of such polymeric materials will depend on the relative mole ratios of the glucose and diacid components and on the reaction conditions employed for the condensation.

EXAMPLE 13

Poly-(1,6-D-glucopyranosyl)ethylmalonates (I, n=5, R=CH$_2$CH$_3$)

Reaction of ethylmalonyl dichloride with 2,3,4-tri-O-benzyl-D-glucopyranose in a mole ratio of 5:6 under the conditions set forth in Examples 1, 3 or 5, followed by removal of the O-benzyl protecting groups under the conditions set forth in Examples 2, 4 or 6 can afford the title compound as a polymeric mixture wherein the average n is five.

Polymers of varying molecular weight may be obtained by suitably adjusting the relative mole ratios of the malonyl dichloride and bifunctional glucose.

EXAMPLE 14

Di-(1,1'-D-glucopyranosyl)linoleylmalonates

Under the conditions and employing the materials set forth in preceding Examples 1 through 4 the title compound can be prepared by substituting linoleylmalonyl dichloride for the n-butylmalonyl and ethylmalonyl dichlorides set forth therein. The resulting compounds di-(1,1'-D-glucopyranosyl)linoleylmalonates will represent those compounds in Formula I where R is alkenyl and have 16 carbon atoms.

Important data concerning water solubility and stability of the products of this invention was secured. Critical for the purpose of biological testing, the product was found to be soluble in water and gave clear solutions. It was stable for prolonged periods (several weeks) at 0° C. in the solid state. After heating at 60° C. for 13 hours, no noticeable degradation resulted (NMR and TLC analysis). Aqueous solutions (1% concentrated) were found to be stable at room temperature for 2–3 days. At 100° C. in water, hydrolysis of the 1,1'-diester to D-glucose and malonic acid was complete in less than one hour.

All of the compounds represented by Formula I can be readily formulated in a nutrient composition formed from an isotonic solution or emulsion for I.V. administration. In those instances where the compounds are not easily dissolved in water, emulsions can be formed utilizing nontoxic, pharmaceutically acceptable emulsifying agents, stabilizers and the like. The resulting solution can be sterilized and administered utilizing the usual I.V. administration equipment.

It will thus be seen that through the present invention there is now provided new compositions of matter which will afford a high caloric source employing the I.V. route of administration. The compounds of this invention will not unduly raise the osmotic pressure yet are readily hydrolyzed and assimilated metabolically. Additionally, the compounds when decarboxylated through enzymatic action result in natural fatty acids providing additional sources of nontoxic calories.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

What is claimed is:

1. A compound of the formula

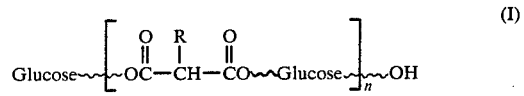

(I)

wherein n is an integer of 1 to 20 and R is hydrogen or an alkyl or alkenyl group of 1 to 20 carbon atoms, and wherein the glucose is attached at the 1-position, the 6-position, or the 1- and 6-positions.

2. A compound as defined in claim 1 wherein said alkyl or alkenyl group contains an even number of carbon atoms.

3. A compound as defined in claim 1 wherein R is an alkyl group containing an even number of carbon atoms.

4. A compound as defined in claim 1 wherein R is an alkenyl group containing an even number of carbon atoms.

5. The compound as defined in claim 1 wherein R is butyl and n is 1.

6. The compound as defined in claim 1 wherein R is ethyl and n is 1.

7. Di-(6,6'-D-glucopyranosyl)malonate.

8. 1,6-Di-O-(1-O-D-glucopyranosyl malonyl)-D-glucopyranose.

9. 1,6-Di-O-(6-O-D-glucopyranosyl malonyl)-D-glucopyranose.

10. The compound as defined in claim 1 wherein R is ethyl and n is 5.

11. The compound as defined in claim 1 wherein R is alkenyl containing 16 carbon atoms.

12. A composition for I.V. administration which is efficiently hydrolyzed, comprising an isotonic aqueous solution or emulsion of a nutritive amount of a compound of the formula

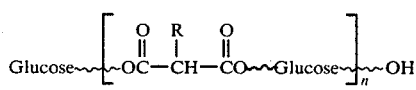 (I)

wherein n is an integer of 1 to 20 and R is hydrogen or an alkyl or alkenyl group of 1 to 20 carbon atoms, and wherein the glucose is attached at the 1-position, the 6-position, or the 1- and 6-positions.

13. The composition as defined in claim 12 wherein said alkyl or alkenyl group contains an even number of carbon atoms.

14. The composition as defined in claim 12 wherein R is an alkyl group containing an even number of carbon atoms.

15. The composition as defined in claim 12 wherein R is an alkenyl group containing an even number of carbon atoms.

16. The composition as defined in claim 12 which contains a mixture of said compounds in which n represents different integers and R represents hydrogen or different alkyl or alkenyl groups.

17. The composition as defined in claim 12 wherein R is butyl and n is 1.

18. The composition as defined in claim 12 wherein R is ethyl and n is 1.

19. The composition as defined in claim 12 wherein said compound is di-(1,1'-glucopyranosyl)ethylmalonate.

20. The composition as defined in claim 12 wherein said compound is di-(1,1'-D-glucopyranosyl)n-butylmalonate.

21. The composition as defined in claim 12 wherein said compound is di-(6,6'-D-glucopyranosyl)malonate.

22. The composition as defined in claim 14 wherein said compound is 1,6-di-O-(1-O-D-glucopyranosyl malonyl)-D-glucopyranose.

23. The composition as defined in claim 14 wherein said compound is 1,6-di-O-(6-O-D-glucopyranosyl malonyl)-D-glucopyranose.

24. The composition as defined in claim 12 wherein R is ethyl and n is on the average, 5.

25. The composition as defined in claim 12 wherein R is alkenyl containing 16 carbon atoms.

26. A composition comprising a mixture of compounds according to claim 1 in which n represents different integers and R represents hydrogen or different alkyl or alkenyl groups.

* * * * *